(12) United States Patent
Drapeau et al.

(10) Patent No.: US 9,526,600 B2
(45) Date of Patent: Dec. 27, 2016

(54) BIODEGRADABLE STENTS AND METHODS FOR TREATING PERIODONTAL DISEASE

(75) Inventors: Susan J. Drapeau, Cordova, TN (US); Daniel Andrew Shimko, Germantown, TN (US); Kelly Brook Emerton, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

(21) Appl. No.: 12/839,940

(22) Filed: Jul. 20, 2010

(65) Prior Publication Data
US 2012/0021370 A1 Jan. 26, 2012

(51) Int. Cl.
| | | |
|---|---|---|
| *A61C 5/00* | (2006.01) | |
| *A61C 19/06* | (2006.01) | |
| *A61C 8/02* | (2006.01) | |
| *A61K 6/00* | (2006.01) | |
| *A61L 31/06* | (2006.01) | |
| *A61L 31/14* | (2006.01) | |
| *A61L 31/16* | (2006.01) | |

(52) U.S. Cl.
CPC ............ *A61C 19/06* (2013.01); *A61C 8/0006* (2013.01); *A61K 6/0044* (2013.01); *A61L 31/06* (2013.01); *A61L 31/148* (2013.01); *A61L 31/16* (2013.01); *A61L 2300/00* (2013.01)

(58) Field of Classification Search
CPC .... A61L 2300/00; A61L 31/148; A61C 19/06; A61C 8/0006; A61K 6/0044
USPC ......... 433/215, 229, 18; 623/1.15, 1.17, 1.2; 606/105; 602/17, 902; 424/435, 422–423, 424/426
See application file for complete search history.

(56) References Cited

U.S. PATENT DOCUMENTS

| | | | |
|---|---|---|---|
| 4,464,114 A | | 8/1984 | Anthony |
| 4,892,736 A | * | 1/1990 | Goodson .............. A61K 9/0063 424/435 |
| 4,961,707 A | | 10/1990 | Magnusson et al. |
| 5,032,445 A | | 7/1991 | Scantlebury et al. |
| 5,059,123 A | | 10/1991 | Jernberg |
| 5,171,148 A | | 12/1992 | Wasserman et al. |
| 5,297,563 A | | 3/1994 | Syers |
| 5,324,294 A | | 6/1994 | Elia et al. |

(Continued)

FOREIGN PATENT DOCUMENTS

| | | |
|---|---|---|
| WO | 0162180 A1 | 8/2001 |
| WO | 2009019629 A2 | 2/2009 |

OTHER PUBLICATIONS

Leghissa GC, Zaffe D, Assenza B, Botticelli AR "Guided bone regeneration using titanium grids: report of 10 cases". Clin Oral Implants Res. Feb. 1999;10(1):62-8 (Abstract).

(Continued)

*Primary Examiner* — Cris L Rodriguez
*Assistant Examiner* — Mirayda A Aponte
(74) *Attorney, Agent, or Firm* — Sorell Lenna & Schmidt LLP

(57) ABSTRACT

The disclosure describes biodegradable stents and methods for selectively guided tissue regeneration in treating a periodontal defect adjacent to a root of a tooth. The biodegradable stents and methods have a coronal portion and a transverse portion or shelf, which reduce unwanted migration of gingival epithelium, gingival connective tissue, and soft tissue and enable the cementum and periodontal ligament cells to re-establish the periodontal ligament in a proper sequence resulting in a new periodontal attachment.

19 Claims, 4 Drawing Sheets

(56) References Cited

U.S. PATENT DOCUMENTS

| | | | |
|---|---|---|---|
| 5,700,479 A * | 12/1997 | Lundgren | A61C 8/00 424/422 |
| 5,727,945 A | 3/1998 | Dannenbaum | |
| 5,769,898 A | 6/1998 | Jisander | |
| 5,839,899 A | 11/1998 | Robinson | |
| 6,031,148 A | 2/2000 | Hayes et al. | |
| 6,155,831 A | 12/2000 | McGuire | |
| 6,478,809 B1 * | 11/2002 | Brotz | A61B 17/00491 606/224 |
| 6,964,566 B2 | 11/2005 | Sapian | |
| 6,976,842 B1 | 12/2005 | Miggantz | |
| 7,105,182 B2 | 9/2006 | Szymaitis | |
| 7,226,612 B2 * | 6/2007 | Sohier et al. | 424/426 |
| 7,322,825 B2 | 1/2008 | Szymaitis | |
| 7,834,527 B2 * | 11/2010 | Alvarez Icaza Rivera et al. | 310/344 |
| 8,034,850 B2 * | 10/2011 | Shalaby | A61K 6/0017 424/602 |
| 2002/0028243 A1 * | 3/2002 | Masters | 424/484 |
| 2003/0212188 A1 | 11/2003 | Tanghe | |
| 2003/0215836 A1 * | 11/2003 | Young et al. | 435/6 |
| 2006/0008773 A1 | 1/2006 | Liao | |
| 2006/0175007 A1 | 8/2006 | Tanghe | |
| 2007/0207444 A1 | 9/2007 | Reynaud et al. | |
| 2008/0019975 A1 * | 1/2008 | Gorman | 424/145.1 |
| 2008/0147197 A1 | 6/2008 | McKay | |
| 2009/0117072 A1 | 5/2009 | Kealey et al. | |
| 2010/0023064 A1 | 1/2010 | Brunger et al. | |
| 2011/0097375 A1 * | 4/2011 | King | A61K 9/0019 424/423 |

OTHER PUBLICATIONS

Degidi M, Scarano A, Piattelli A. "Regeneration of the alveolar crest using titanium micromesh with autologous bone and a resorbable membrane". J Oral Implantol. 2003;29(2):86-90 (Abstract).

Cetiner D, Bodur A, Uraz A. "Expanded mesh connective tissue graft for the treatment of multiple gingival recessions"., J Periodontol. Aug. 2004; 75(8):1167-72 (Abstract).

De Toledo Lourenço AH, de Toledo Lourenço E Jr, Fraga MR, Vitral RW. "The association of a polydioxanone tent without a guided tissue regeneration membrane to a coronal sliding flap for root coverage". J Periodontol. Oct. 2009; 80(10):1674-9 (Abstract).

Jovanovic SA, Nevins M. "Bone formation utilizing titanium-reinforced barrier membranes". Int J Periodontics Restorative Dent. Feb. 1995;15(1):56-69 (Abstract).

Towfighi P, Arnold R.Compend Contin Educ Dent. "Use of a titanium-reinforced membrane in periodontal regeneration: a case report". Sep. 1995;16(9):920, 922, 924 passim; quiz 928 (Abstract).

Tinti C, Manfrini F, Parma-Benfenati S. "A bioresorbable barrier in the treatment of gingival recession: description of a new resorbable dome device". Int J Periodontics Restorative Dent. Feb. 2001;21(1):31-9 (Abstract).

International Search Report and Written Opinion for PCT/US2011/044064, the counterpart application mailed on Mar. 9, 2012.

* cited by examiner

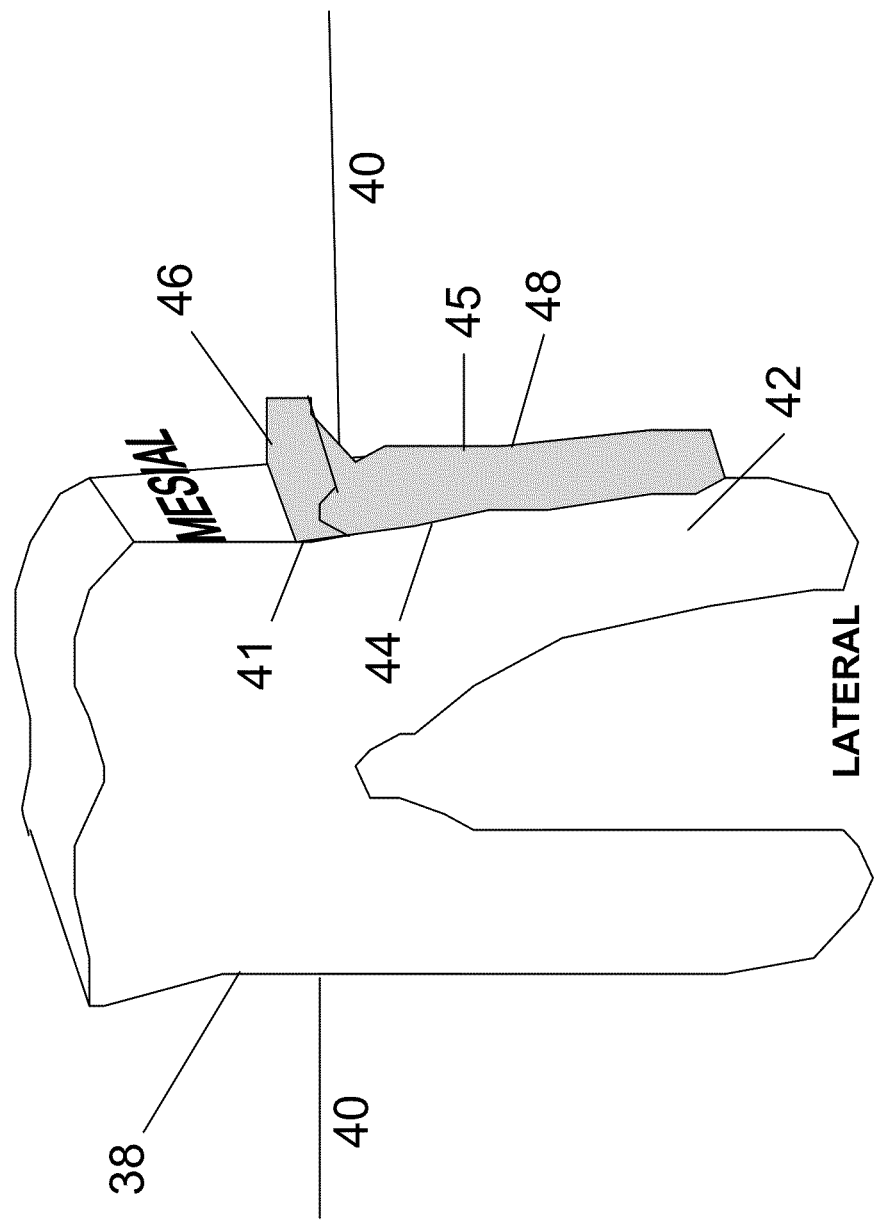

BIODEGRADABLE STENTS AND METHODS FOR TREATING PERIODONTAL DISEASE

BACKGROUND

During the early stages of periodontal disease, known commonly as gingivitis, bacteria on the teeth and near the gingiva infect and irritate the sulcus where the gingiva approximates the tooth. The presence of bacteria can lead to destruction of the gingival epithelium which connects the gingiva to the tooth and can force the epithelium to separate from the root of the tooth. Also, as a result of bacterial presence, inflammatory cells increasingly populate the gingival tissues. Thus, the tissue is weaker due to the disease, and attachment is lessened. Of course, further infection moves the tissue attachment further toward the apex of the tooth, creating a pathological pocket much deeper than the normal sulcus.

Naturally, this pocket is difficult to clean or floss because the routine cleaning instruments of normal home care cannot reach the bacteria or plaque, which accumulate within the pocket. As disease extends the pocket, the periodontal ligament which attaches the tooth to the supporting bone, and the supporting alveolar bone itself, are destroyed. This disease leaves a periodontal defect, filled with plaque and bacteria. Ultimately, the tooth could be surrounded by loose, diseased, and detached gingiva. Eventually such deterioration can result in the loss of the tooth.

One conventional treatment of periodontal defects involves surgically gaining access to the tooth root surface in an effort to remove bacteria and possible infected soft tissue and to alter the periodontal pocket or obtain reattachment of the connective tissue toward the crown of the tooth. Some of the former methods accomplish this attachment by cutting away gingival tissue near the crown of the tooth and, if necessary, shaping underlying bone to create a sulcus similar in depth to a normal sulcus so that regular oral hygiene may be used to maintain attachment of the gingiva to the tooth. Of course, such treatment does not recreate the attachment of the gingiva near the crown like that which existed before any diseased condition. Such treatment also does not replace any periodontium lost to disease.

Another conventional surgical treatment for periodontal disease is known as a gingival flap procedure. One or more flaps of gingival tissue are retracted from the tooth. After the tooth root is thoroughly cleaned, and diseased soft tissue is removed, these flaps are reopposed to the tooth. In some instances gingival grafts from other portions of the mouth are incorporated. Reattachment is unpredictable using this procedure. This is because gingival epithelium migrates rapidly along a tooth root toward the apex of the tooth, and bone cementum, and periodontal ligament migrate much more slowly. If the gingival epithelium is allowed to migrate toward the base of the periodontal defect, the gingival tissue is said to undergo a process called repair. The more desired process would allow the bone, cementum, and periodontal ligament cells to migrate coronally; this process is called regeneration. Repair is simply healing but regeneration is healing of the defect with the return of the defect towards the original condition.

Typically, after periodontal surgery, a race begins among the cells from the four types of periodontal tissues, gingival epithelium, gingival connective tissue, alveolar bone and periodontal ligament, to repopulate the previously diseased root surface.

If uncontrolled, the healing process usually results in downgrowth of cells from the gingival epithelium along the surface of the gingival connective tissue immediately lateral to the root surface, which prevents migration of cementoblasts from the adjacent periodontal ligament to form new cementum on the denuded root surface to which new periodontal fibers can attach. Even if the gingival connective tissue, also quick to take part in the healing process, occupies the space immediately lateral to the root surface and hinders the downgrowth of epithelial cells, there will be no true new attachment between that type of tissue and the root surface but rather a substantial risk of root resorption.

If the alveolar bone, which usually regenerates more slowly than the gingival epithelium and connective tissue, happens to fill up parts of the space adjacent to the root surface and reaches the root surface, the bone will form an ancylotic union with the part of the root which is unprotected by root cementum and periodontal ligament tissue.

If, on the other hand, cement-producing cells, e.g., cementoblasts from the remaining adjacent and intact periodontal ligament tissue, reach the denuded root surface area, they will desirably produce cementum with inserting connective tissue fibers on the dentine surface, e.g., a true, new periodontal ligament is formed uniting the root with the surrounding bone and gingival connective tissue.

Unfortunately, the cementoblasts do not normally reach more than a negligible part of the previously diseased root surface immediately adjacent to the intact periodontal ligament due to the fact that cells of the other tissues (e.g., gingival epithelium, gingival connective tissue, soft tissue, etc.) occupy the wound area.

Therefore, there is a need for devices and methods that utilize guided tissue regeneration where the cementum and periodontal ligament producing cells have the ability to become established on the root surface by maintaining space and isolating the root surface from other tissues during healing. This isolation during the initial healing process will reduce migration of gingival epithelium and enable the periodontal ligament to become re-established in a proper sequence resulting in a new periodontal attachment.

SUMMARY

Devices and methods are provided that utilize guided tissue regeneration where the cementum and periodontal ligament producing cells have the ability to become established on the root surface by maintaining space and isolating the root surface from other tissues during healing.

In some embodiments, the devices and methods will reduce unwanted migration of gingival epithelium, gingival connective tissue, fibrous/scar tissue, granulation tissue or soft tissue and enable the cementum and periodontal ligament cells to re-establish the periodontal ligament in a proper sequence resulting in a new periodontal attachment.

In one embodiment, there is a biodegradable stent for selectively guided tissue regeneration in treating a periodontal defect adjacent to a root of a tooth, the biodegradable stent comprising a coronal portion and a transverse portion, the coronal portion having a first surface configured to contact at least a portion of the root of the tooth and a second surface configured to contact at least a portion of the periodontal defect, the transverse portion above the coronal portion and substantially perpendicular to it, the transverse portion having a first surface configured to contact a portion of the tooth and a second surface configured to extend away from the tooth and over a portion of the periodontal defect to maintain a space between gingival epithelium tissue and periodontal ligament tissue including the periodontal defect, wherein the biodegradable stent reduces ingrowth of gingival epithelium cells and permits ingrowth of periodontal ligament cells.

In another embodiment, there is a biodegradable stent for selectively guided tissue regeneration in treating a periodontal defect adjacent to a root of a tooth, the biodegradable stent comprising a coronal portion and a transverse portion, the coronal portion having a first surface configured to contact at least a portion of the root of the tooth and a second surface configured to contact at least a portion of the periodontal defect, the transverse portion above the coronal portion and substantially perpendicular to it, the transverse portion having a first surface configured to contact a portion of the tooth and a second surface configured to extend away from the tooth and over a portion of the periodontal defect to maintain a space between gingival epithelium tissue and periodontal ligament tissue including the periodontal defect, a band extending over the tooth and contacting the second surface of the coronal portion and/or the transverse portion of the stent so as to hold the stent in place, wherein the biodegradable stent reduces ingrowth of gingival epithelium cells and permits ingrowth of periodontal ligament cells.

In yet another embodiment, there is a method for selectively guided tissue regeneration in treating a periodontal defect adjacent to a root of a tooth, the method comprising affixing to the tooth a biodegradable stent that maintains a space between gingival epithelium tissue and periodontal ligament tissue including the periodontal defect, the biodegradable stent comprising a coronal portion and a transverse portion, the coronal portion having a first surface configured to contact at least a portion of the root of the tooth and a second surface configured to contact at least a portion of the periodontal defect, the transverse portion above the coronal portion and substantially perpendicular to it, the transverse portion having a first surface configured to contact a portion of the tooth and a second surface configured to extend away from the tooth and over a portion of the periodontal defect, wherein the biodegradable stent reduces ingrowth of gingival epithelium cells and permits ingrowth of periodontal ligament cells.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

FIG. 2 is a schematic partially front view of an embodiment of a tooth where the periodontal defect has healed and a stent is affixed adjacent to the healed periodontal defect.

Figure 1B:
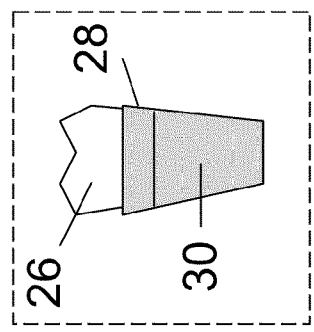
FIG. 1B is a schematic side view of an embodiment of a tooth having a stent affixed to the mesial plane of the tooth.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Definitions

It is noted that, as used in this specification and the appended claims, the singular forms "a," "an," and "the," include plural referents unless expressly and unequivocally limited to one referent. Thus, for example, reference to "a biodegradable stent" includes one, two, three or more biodegradable stents.

The term "practitioner" or "user" means a person who is using the methods and/or devices of the current disclosure on the patient. This term includes, without limitation, doctors (e.g., surgeons, interventional specialists, physicians), nurses, nurse practitioners, other medical personnel, clinicians, dentists, veterinarians, or scientists.

The term "mammal" refers to organisms from the taxonomy class "mammalian," including but not limited to humans, other primates such as chimpanzees, apes, orangutans and monkeys, rats, mice, cats, dogs, pigs, cows, horses, etc. In various embodiments, the mammal is a human patient.

The term "transverse" includes horizontal or at right angles or perpendicular to a long axis. Substantially perpendicular includes angles that are 55, 50, 45, 40, 35 or 30 degrees.

The term "coronal" includes vertical or a vertical plane that divides the object into first and second surfaces.

"Periodontal disease" includes any condition that affects the gums and other structures supporting the teeth. The most common form of periodontal disease is caused by bacterial infections. These bacteria grow in a sticky film called dental plaque that sticks on the tooth surfaces next to the gums. The bacteria can cause inflammation, spread and destroy the gums and the supporting bone around the teeth. The mildest form of periodontal disease is gingivitis, which affects only the gums. More severe periodontal disease damages the other supporting structures including the periodontal ligament and/or bone structure of the tooth or alveolar bone.

The term "stent" means a material or device used for separating tissue and holding it in such separated position.

The term "therapeutic agent" may be used interchangeably herein with the terms "drug," "therapeutically effective amount," and "active pharmaceutical ingredient" or "API." It will be understood that unless otherwise specified a "therapeutic agent" formulation may include more than one therapeutic agent, wherein exemplary combinations of therapeutic agents include a combination of two or more drugs. The therapeutic agent provides a concentration gradient of the therapeutic agent for delivery to the site.

A "therapeutically effective amount" or "effective amount" is such that when administered, the drug results in alteration of the biological activity, such as, for example, inhibition of inflammation, reduction or alleviation of periodontal disease, etc.

The term "biodegradable" includes that all or parts of the stent will degrade over time by the action of enzymes, by hydrolytic action and/or by other similar mechanisms in the oral cavity. In various embodiments, "biodegradable" includes that the stent or part of the stent (e.g., microparticle, microsphere, etc. incorporated into the stent) can break down or degrade within the oral cavity to non-toxic components after or while a therapeutic agent has been or is being released. By "bioerodible" it is meant that the stent or portion thereof will erode or degrade over time due, at least in part, to contact with substances found in the surrounding tissue, fluids or by cellular action. By "bioresorbable" it is meant that the stent or portion thereof will be broken down and resorbed within the human body, for example, by a cell or tissue. "Biocompatible" means that the stent will not cause substantial tissue irritation or necrosis at the target tissue site.

The phrases "sustained release" and "sustain release" (also referred to as extended release or controlled release) are used herein to refer to one or more therapeutic agent(s) that is introduced into the oral cavity of a human or other mammal and continuously or continually releases a stream of one or more therapeutic agents over a predetermined time period and at a therapeutic level sufficient to achieve a desired therapeutic effect throughout the predetermined time period.

The phrase "immediate release" is used herein to refer to one or more therapeutic agent(s) that is introduced into the oral cavity and that is allowed to dissolve in or become absorbed at the location to which it is administered, with no intention of delaying or prolonging the dissolution or absorption of the drug.

"Treating" or "treatment" of a disease or condition refers to executing a protocol that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes protocols that have only a marginal effect on the patient. Treatment can include inhibiting the disease, e.g., arresting its development; or relieving the disease, e.g., causing regression of the disease. For example, treatment can include reducing acute or chronic inflammation; alleviating pain and mitigating and inducing re-growth of new periodontal ligament, bone and other tissues; as an adjunct in orthognathic surgery; any elective cosmetic surgical or repair procedure or so forth.

Biodegradable Stents

Devices and methods are provided that utilize guided tissue regeneration where the cementum and periodontal ligament producing cells have the ability to become established on the root surface by maintaining space and isolating the root surface from other tissues during healing. The devices and methods provided selectively guide these cell types to the periodontal defect, which improves its repair.

In some embodiments, the devices and methods will reduce unwanted migration of gingival epithelium and enable the periodontal ligament to become re-established in a proper sequence resulting in a new periodontal attachment.

In one embodiment, there is a biodegradable stent for selectively guided tissue regeneration in treating a periodontal defect adjacent to a root of a tooth, the biodegradable stent comprising a coronal portion and a transverse portion, the coronal portion having a first surface configured to contact at least a portion of the root of the tooth and a second surface configured to contact at least a portion of the periodontal defect, the transverse portion above the coronal portion and substantially perpendicular to it, the transverse portion having a first surface configured to contact a portion of the tooth and a second surface configured to extend away from the tooth and over a portion of the periodontal defect to maintain a space between gingival epithelium tissue and periodontal ligament tissue including the periodontal defect, wherein the biodegradable stent reduces ingrowth of gingival epithelium cells and permits ingrowth of periodontal ligament cells.

Figure 1C:
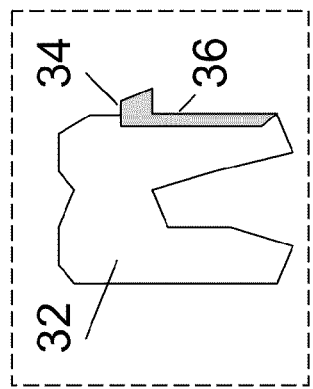
FIG. 1C is a schematic lateral front view of an embodiment of a tooth having a stent affixed to it.
Figure 1A:
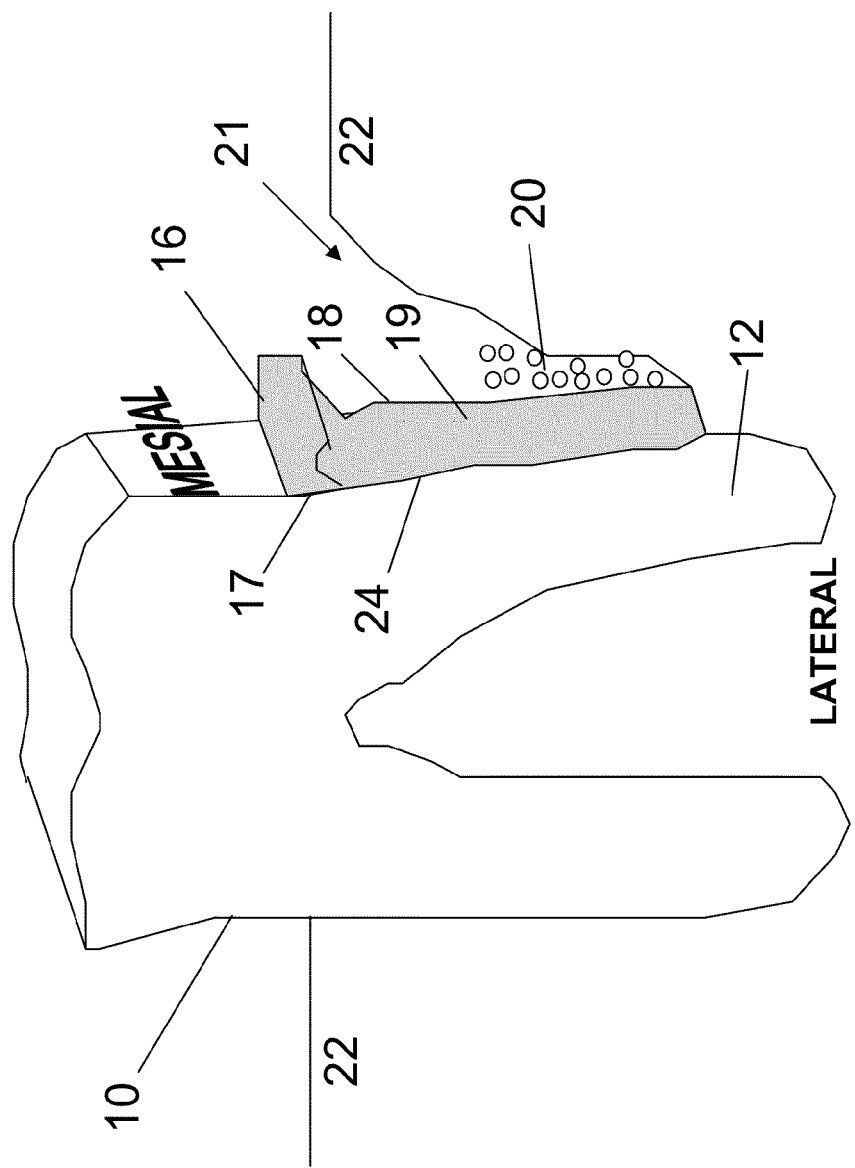
FIG. 1A is a schematic partially front view of an embodiment of a tooth having a periodontal defect and a stent affixed adjacent to the periodontal defect.

Referring to FIG. 1A, it is a schematic partially front view of an embodiment of a tooth having a periodontal defect and a stent affixed adjacent to the periodontal defect. In this illustration, a tooth 10 has periodontal ligament 22 adjacent to it. However, there is a periodontal defect 21 that is adjacent to (or next to) root 12. The periodontal defect includes absence or little presence of bone, periodontal ligament and/or cementum. The periodontal tissue may also contain inflamed tissue, granulation tissue and/or bacteria. A biodegradable stent 18 comprising a coronal portion having a first surface 24 is attached to the tooth root, for example, by an adhesive. The first surface 24 of the coronal portion conforms or coapts to the surface of part or all of the tooth and/or tooth root. The second surface 19 of the coronal portion contacts at least a portion of the periodontal defect 21. The coronal portion acts by maintaining space and isolating the root surface from other tissues (e.g., gingival epithelium, gingival connective tissue, other soft tissue) during healing. This space and isolation during the initial healing process will reduce migration of gingival epithelium cells, gingival connective tissue cells, and/or other soft tissue cells and enables the periodontal ligament 22 to become re-established in a proper sequence resulting in a new periodontal attachment. The biodegradable stent also comprises a transverse portion above the coronal portion and substantially perpendicular to it. The transverse portion is shown as a shelf. The transverse portion has a first surface 17 configured to contact a portion of the tooth. Here the first surface 17 of the transverse portion conforms or coapts to the surface of part or all of the tooth just above the root.

The transverse portion also comprises a second surface 16 configured to extend away from the tooth and over a portion of the periodontal defect to maintain a space between gingival epithelium tissue and periodontal ligament tissue including the periodontal defect 21. The transverse portion creates a shelf during the initial healing process that will reduce migration of gingival epithelium cells, gingival connective tissue cells, and/or other soft tissue cells and enables the periodontal ligament 22 to become re-established in a proper sequence resulting in a new periodontal attachment. In the embodiment shown, as the stent degrades, cementum cells, periodontal ligament producing cells and alveolar bone cells (shown collectively as 20) migrate in and permit ingrowth of periodontal ligament and alveolar bone to repair the periodontal defect. In some embodiments, bone cells, or bone replacement materials can be placed in the periodontal defect 21 to assist in the repair.

Like the coronal portion, the transverse portion acts by maintaining space and isolating the tooth surface from other tissues (e.g., gingival epithelium, gingival connective tissue, other soft tissue) during healing. This space and isolation during the initial healing process will reduce migration of gingival epithelium cells, gingival connective tissue cells, and/or other soft tissue cells and enables the periodontal ligament 22 to become re-established in a proper sequence resulting in a new periodontal attachment. It should be understood by one of ordinary skill in the art that the stent can be one piece and has the coronal portion and transverse portion as one piece. Alternatively, the coronal portion and the transverse portion can be two separate pieces that are attached together by any attachment means, adhesive, snap-fit junction, push fitting, mating pairs, screw and thread fitting, etc. It will be understood that more than one stent can be used to treat periodontal disease. For example, one stent can be affixed to each side of the tooth at or near each tooth root.

FIG. 1B is a schematic side view of an embodiment of a tooth 26 having a stent with a transverse portion or shelf 28 and a coronal portion 30 affixed to the mesial plane or middle of the tooth. Here the stent is porous and has a pore size of from about 10 µm to about 200 µm to allow cementum cells, periodontal ligament producing cells and alveolar bone cells in and keep gingival epithelium, gingival connective tissue, other soft tissue cells out. Of course as the stent degrades the influx of cells will increase, but this will be done in sequence for proper repair of the periodontal defect. In some embodiments, the stent comprises an anti-adhesive coating or non-proliferative factor to prevent attachment of microorganisms (e.g., bacteria and/or fungi) or reduce or prevent attachment of gingival epithelium, gingival connective tissue, fibrous/scar tissue, granulation tissue and/or soft tissue to the stent. Some examples of anti-adhesive agents, include, antimicrobials, fluorinated monomers, such as e.g. perfluorinated alkyl methacrylates or the like.

In some embodiments, the transverse portion can be non-porous to prevent attachment of microorganisms (e.g., bacteria and/or fungi) or reduce or prevent attachment of gingival epithelium, gingival connective tissue, fibrous/scar tissue, granulation tissue and/or soft tissue to the stent and the coronal portion or depth portion of the stent can be porous.

In some embodiments, 0.1-20 mm, or 0.5 to 5 mm of space can be maintained between the periodontal defect (e.g., periodontal defect, native bone) and the tented gingival epithelium cells, gingival connective tissue cells, and/or other soft tissue cells. In some embodiments, the stent has a thickness of from about 500 µm to 2 mm. In some embodiments, the length, depth, and/or width of each stent may range from about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm to about 20 mm. In some embodiments, the thickness of each stent can be 0.5 mm, 1 mm, 2 mm, 3 mm, 4 mm or 5 mm in thickness. The practitioner can modify these dimensions if needed.

FIG. 1C is a schematic lateral front view of an embodiment of a tooth 32 having a stent affixed to it. The stent has transverse portion or shelf 34 that extends away from the tooth and is located just under the tooth crown. The stent also comprises coronal portion 36. The stent conforms to part of the surface of the tooth and is affixed to the tooth root by an adhesive.

Referring to FIG. 2, it is a schematic partially front view of an embodiment of a tooth 38 having a repaired periodontal ligament 40, where the periodontal defect has been healed. The stent is affixed adjacent to the tooth and the tooth root 42. In this illustration, a biodegradable stent 45 comprising a coronal portion having a first surface 44 is attached to the tooth root, for example, by an adhesive. The first surface 44 of the coronal portion conforms or coapts to the surface of part or all of the tooth and/or tooth root. The second surface 48 of the coronal portion contacts at least a portion of the periodontal ligament 40. The coronal portion acts by maintaining space and isolating the root surface from other tissues (e.g., gingival epithelium, gingival connective tissue, other soft tissue) during healing. This space and isolation during the initial healing process will reduce migration of gingival epithelium cells, gingival connective tissue cells, and/or other soft tissue cells and enables the periodontal ligament 40 to become re-established (as shown)

in a proper sequence resulting in a new periodontal attachment. The biodegradable stent also comprises a transverse portion above the coronal portion and substantially perpendicular to it. The transverse portion is shown as a shelf. The transverse portion has a first surface 41 configured to contact a portion of the tooth. Here the first surface of the transverse portion conforms or coapts to the surface of part or all of the tooth just above the root.

The transverse portion also comprises a second surface 46 configured to extend away from the tooth and over a portion of the periodontal defect to maintain a space between gingival epithelium tissue and periodontal ligament tissue including the periodontal defect. The transverse portion creates a shelf during the initial healing process that will reduce migration of gingival epithelium cells, gingival connective tissue cells, and/or other soft tissue cells and enables the periodontal ligament to become re-established (which has now healed and is shown as 40) in a proper sequence resulting in a new periodontal attachment. It will be understood by those of ordinary skill in the art that the stent will degrade and at the time that the stent is partially or completely degraded, the periodontal defect will be healed and, because the stent is biodegradable, in some embodiments, there will be no need for a separate procedure to be scheduled to remove the stent. In the embodiment shown, as the stent degrades, cementum cells, periodontal ligament producing cells and alveolar bone cells migrate in and permit ingrowth of periodontal ligament and alveolar bone to repair the periodontal defect. It will be understood by those of ordinary skill in the art that all or portions of the stent can have one or more therapeutic agents disposed within or on its surface. As the biodegradable stent degrades, the stent releases the therapeutic agent.

Figure 3B:
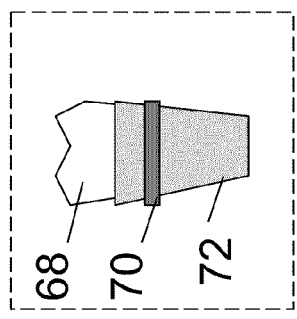
FIG. 3B is a schematic side view of an embodiment of a tooth having a stent affixed to the mesial plane of the tooth using an elastic band.
Figure 3C:
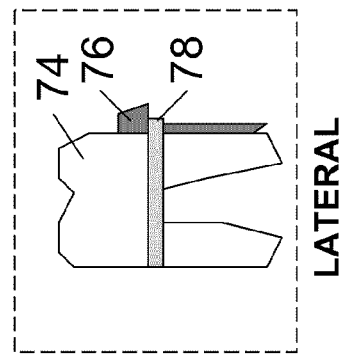
FIG. 3C is a schematic lateral front view of an embodiment of a tooth having a stent affixed to it using an elastic band.
Figure 3A:
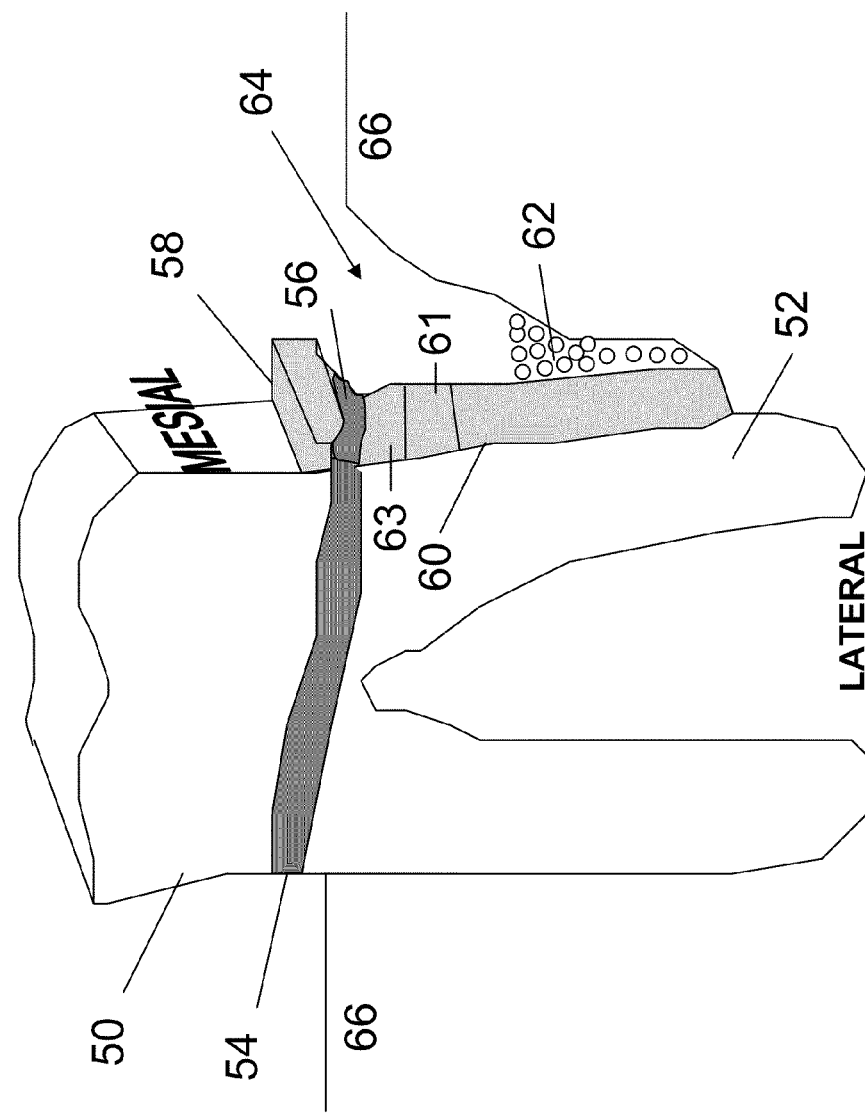
FIG. 3A is a schematic partially front view of an embodiment of a tooth having a periodontal defect and a stent affixed adjacent to the periodontal defect using an elastic band.

Referring to FIG. 3A, it is a schematic partially front view of an embodiment of a tooth having a periodontal defect and a stent affixed adjacent to the periodontal defect. In this illustration, a tooth 50 has periodontal ligament 66 adjacent to it. However, there is a periodontal defect 64 that is adjacent to (or next to) root 52. A biodegradable stent 60 comprising a coronal portion having a first surface 63 that is attached to the tooth root, for example, by an elastic band 54. The elastic band 54 runs across the tooth and holds the biodegradable stent 60 in place. For example, the elastic band can fit below the crown and wrap around the tooth. The elastic band 54 can be coated on its interior side with an adhesive to further hold the biodegradable stent in portion. In some embodiments, the band can also be coated with a therapeutic agent (e.g., antibiotic, analgesic, anti-inflammatory agent, growth factor, or other agent) on its interior or exterior sides or both.

In other embodiments, the band can be constructed to have bacteria wicking action to prevent bacterial growth. In some embodiments, the elastic band extends across the surface of the tooth and contacts the biodegradable stent at the second surface of the coronal portion of the stent and just under the transverse portion or shelf 58. In some embodiments, the stent has a channel 56 configured to receive the elastic band 54 by constricting the stent against the tooth. This channel aids in allowing the band to hold the stent in place. It will be understood that the band, in some embodiments, can also contact the transverse portion of the stent 58. In some embodiments, to insure that the stent is held in place the stent can be affixed to the tooth by an adhesive disposed on the first side of the stent in addition to the elastic band.

The first surface 63 of the coronal portion conforms or coapts to the surface of part or all of the tooth and/or tooth root. The first surface may contain a therapeutic agent that may, for example, have a zone that releases the therapeutic agent immediately or in a sustained manner. The zone may release, for example, an agent that inhibits gingival epithelium, gingival connective tissue, or other soft tissue. This zone may be positioned at the top, middle and/or bottom of the stent.

The second surface 61 of the coronal portion contacts at least a portion of the periodontal defect 64. The coronal portion acts by maintaining space and isolating the root surface from other tissues (e.g., gingival epithelium, gingival connective tissue, other soft tissue) during healing. This space and isolation during the initial healing process will reduce migration of gingival epithelium cells, gingival connective tissue cells, and/or other soft tissue cells and enables the periodontal ligament 66 to become re-established in a proper sequence resulting in a new periodontal attachment. In some embodiments, the second surface of the coronal portion may comprise a therapeutic agent that may, for example, be in a zone that releases the therapeutic agent immediately or in a sustained manner. The zone may release, for example, an agent that enhances cementum cells, periodontal ligament producing cells and alveolar bone cells that migrate in and permit ingrowth of periodontal ligament and alveolar bone to treat the periodontal defect. This zone may be positioned at the top, middle and/or bottom of the stent.

The biodegradable stent also comprises a transverse portion 58 above the coronal portion 63 and substantially perpendicular to it. The transverse portion 58 is shown as a shelf. The transverse portion has a first surface configured to contact a portion of the tooth. Here the first surface of the transverse portion conforms or coapts to the surface of part or all of the tooth just above the root.

The transverse portion 58 also comprises a second surface configured to extend away from the tooth and over a portion of the periodontal defect to maintain a space between gingival epithelium tissue and periodontal ligament tissue including the periodontal defect 64. The transverse portion creates a shelf during the initial healing process that will reduce migration of gingival epithelium cells, gingival connective tissue cells, and/or other soft tissue cells and enables the periodontal ligament 64 to become re-established in a proper sequence resulting in a new periodontal attachment. In the embodiment shown, as the stent degrades, cementum cells, periodontal ligament producing cells and alveolar bone cells migrate in and permit ingrowth of periodontal ligament and alveolar bone to treat the periodontal defect. In some embodiments, bone replacement materials 62 can be placed in the periodontal defect 64 to assist in the repair. Like the stent, and band, the bone replacement material may contain a therapeutic agent that allows sustained and/or immediate release of the therapeutic agent.

Like the coronal portion, the transverse portion acts by maintaining space and isolating the tooth surface from other tissues (e.g., gingival epithelium, gingival connective tissue, other soft tissue) during healing. This space and isolation during the initial healing process will reduce migration of gingival epithelium cells, gingival connective tissue cells, and/or other soft tissue cells and enables the periodontal ligament 66 to become re-established in a proper sequence resulting in a new periodontal attachment.

FIG. 3B is a schematic side view of an embodiment of a tooth 68 having a stent with a transverse portion or shelf and a coronal portion 72 affixed to the mesial plane of the tooth using an elastic band 70.

FIG. 3C is a schematic lateral front view of an embodiment of a tooth 74 having a stent affixed to it. The stent has transverse portion or shelf 76 that extends away from the tooth and is located just under the tooth crown. The stent also comprises coronal portion. The stent conforms to part of the surface of the tooth and is affixed to the tooth root using an elastic band 78 that is disposed just under shelf 76. The elastic band can be removable and the practitioner or patient can remove the band and place a new one, if desired. Although, one band is shown, it will be understood that one, two, three, four, or more bands can be used. Likewise, although one stent is shown, it will be understood that one, two, three, four, or more stents can be used in or adjacent to the periodontal defect.

Figure 4:
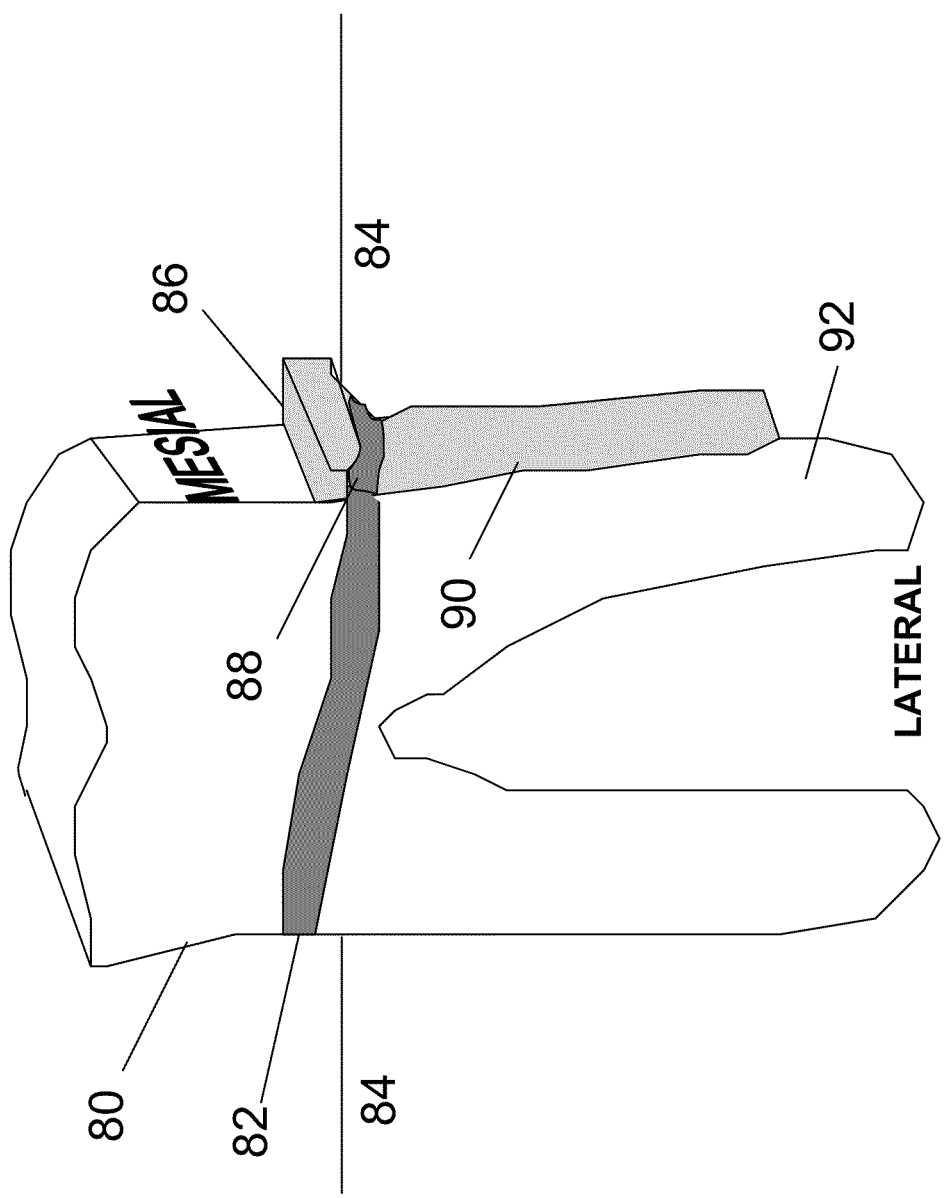
FIG. 4 is a schematic partially front view of an embodiment of a tooth where the periodontal defect has healed and a stent is affixed adjacent to the healed periodontal defect using an elastic band.

Referring to FIG. 4, it is a schematic partially front view of an embodiment of a tooth 80 having a repaired periodontal ligament 84, where the periodontal defect has been healed. The stent is affixed adjacent to the tooth and the tooth root 92. In this illustration, a biodegradable stent comprising a coronal portion 90 having a first surface is attached to the tooth root, for example, by an elastic band 82. The elastic band 82 runs across the tooth and holds the biodegradable stent in place. The elastic band 82 can be coated on its interior side with an adhesive to further hold the biodegradable stent in position. In some embodiments, the band can also be coated with a therapeutic agent (e.g., antibiotic, analgesic, anti-inflammatory agent, growth factor, or other agent) on its interior or exterior sides or both. In other embodiments, the band can be constructed to have bacteria wicking action to prevent bacterial growth. In some embodiments, the band is made from non-biodegradable material. In some embodiments, the elastic band extends across the surface of the tooth and contacts the biodegradable stent at the second surface of the stent and just under the transverse portion or shelf 86.

In some embodiments, the stent has a channel 88 configured to receive the elastic band 82. This channel aids in allowing the band to hold the stent in place. It will be understood that the band can also contact the transverse portion of the stent 86. In some embodiments, to insure that the stent is held in place, the stent can be affixed to the tooth by an adhesive disposed on the first side of the stent in addition to the elastic band. Although a band is shown, it will be understood by those of ordinary skill in the art that the stent can be attached to the tooth by other affixing means, such as for example, a strip, wire, clip, suture, post, or the like.

The first surface of the coronal portion conforms or coapts to the surface of part or all of the tooth and/or tooth root. The second surface of the coronal portion contacts at least a portion of the periodontal ligament 84. The coronal portion acts by maintaining space and isolating the root surface from other tissues (e.g., gingival epithelium, gingival connective tissue, other soft tissue) during healing. This space and isolation during the initial healing process will reduce migration of gingival epithelium cells, gingival connective tissue cells, and/or other soft tissue cells and enables the periodontal ligament 84 to become re-established (as shown) in a proper sequence resulting in a new periodontal attachment. The biodegradable stent also comprises a transverse portion 86 above the coronal portion and substantially perpendicular to it. The transverse portion is shown as a shelf. The transverse portion has a first surface configured to contact a portion of the tooth. Here the first surface of the transverse portion conforms or coapts to the surface of part or all of the tooth just above the root.

The transverse portion also comprises a second surface configured to extend away from the tooth and over a portion of the periodontal defect to maintain a space between gingival epithelium tissue and periodontal ligament tissue including the periodontal defect. The transverse portion creates a shelf during the initial healing process that will reduce migration of gingival epithelium cells, gingival connective tissue cells, and/or other soft tissue cells and enables the periodontal ligament to become re-established (which has now healed and is shown as 84) in a proper sequence resulting in a new periodontal attachment. In some embodiments, the stent allows growth of the periodontal ligament both horizontally and/or vertically.

In some embodiments, in use for the treatment of periodontal disease, (a) a sharp dissection of the gum tissues overlying the bony defect component of the periodontal lesion is made, (b) debridement of the periodontal lesion is then performed, which results in an exposed bony pocket; (c) the stent is then placed at or near the exposed boney pocket, (d) the periodontal lesion is optionally filled with bone replacement material (e.g., bone graft material), and (e) the gum tissue can be closed by suturing the gum tissue in apposition to the stent such that the transverse portion of the stent is visible in the mouth and above the margin of gum line or the gum tissue can be pulled over the transverse portion of the stent and sutured in apposition to the tooth itself.

In some embodiments, the stent can be rigid, or flexible or a combination thereof. The stent can be any shape in a determined or regular form or configuration in contrast to an indeterminate or vague form or configuration (as in the case of a lump or other solid mass of no special form). Some shapes of the stent include, square, rectangular, triangular, circular, spherical, substantially spherical, rod shaped, oval, or the like. The stent can be regular, geometric shapes to irregular, angled, or non-geometric shapes, or combinations of features having any of these characteristics. In some embodiments, the transverse portion of the stent is longer, shorter or the same size as the coronal portion of the stent.

In some instances, it may be desirable to avoid having to remove the stent and/or band. In those instances, the stent and/or band may comprise a biodegradable material. There are numerous materials available for this purpose and having the characteristic of being able to breakdown or disintegrate over a prolonged period of time when positioned in the oral cavity. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the stent and/or band (homogeneous or bulk erosion).

In various embodiments, the stent and/or band may comprise a bioerodable, a bioabsorbable, and/or a biodegradable biopolymer that may provide immediate release, or sustained release of the therapeutic agent. Examples of suitable polymers that the stent and/or band can be made of include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, .-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations.

In various embodiments, the stent and/or band comprises poly(lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone or a combination thereof.

As persons of ordinary skill in the art are aware, an implantable stent and/or band compositions having a blend of polymers with different end groups if used in the resulting formulation will have a lower burst index and a regulated duration of delivery of the therapeutic agent. For example, one may use polymers with acid (e.g., carboxylic acid) and ester end groups (e.g., methyl of ethyl ester end groups) to provide sustained release or allow the stent to degrade over a longer period of time.

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting stent and/or band having a regulated burst index and duration of delivery of the therapeutic agent. For example, a stent and/or band composition having a polymer with a L/G ratio of 50:50 may have a short duration of delivery ranging from about two days to about one month; a stent and/or band composition having a polymer with a L/G ratio of 65:35 may have a duration of delivery of about two months; a stent and/or band composition having a polymer with a L/G ratio of 75:25 or L/CL ratio of 75:25 may have a duration of delivery of about three months to about four months; a stent and/or band composition having a polymer ratio with a L/G ratio of 85:15 may have a duration of delivery of about five months; a stent and/or band composition having a polymer with a L/CL ratio of 25:75 or PLA may have a duration of delivery greater than or equal to six months; a stent and/or band composition having a terpolymer of CL/G/L with G greater than 50% and L greater than 10% may have a duration of delivery of about one month and a stent and/or band composition having a terpolymer of CL/G/L with G less than 50% and L less than 10% may have a duration for months up to six months. In general, increasing the G content relative to the CL content shortens the duration of delivery whereas increasing the CL content relative to the G content lengthens the duration of delivery. Thus, among other things, stent and/or band compositions having a blend of polymers having different molecular weights, end groups and comonomer ratios can be used to create a stent and/or band formulation having a lower initial burst and a regulated duration of delivery.

In some embodiments, the stent can comprise autograft, allograft, xenogenic, or natural tissue.

Gels

The stent and/or band may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate, calcium or calcium salts such as calcium carbonate, calcium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers.

In various embodiments, the stent and/or band is a gel. The gel may have a pre-dosed viscosity in the range of about 1 to about 500 centipoises (cps), 1 to about 200 cps, or 1 to about 100 cps. After the gel is administered to the target site, the viscosity of the gel will increase and the gel will have a modulus of elasticity (Young's modulus) in the range of about $1 \times 10^4$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In one embodiment, the stent comprises an adherent gel that can be evenly distributed throughout the oral cavity by the periodontal area. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. With the gel, the user can create the stent having the shelf at the periodontal site.

The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or to adhere to the target tissue.

In various embodiments, a gel is provided that hardens or stiffens after delivery. Typically, hardening gel formulations may have a pre-dosed modulus of elasticity in the range of about $1 \times 10^4$ to about $3 \times 10^5$ dynes/cm$^2$, or $2 \times 10^4$ to about $2 \times 10^5$ dynes/cm$^2$, or $5 \times 10^4$ to about $1 \times 10^5$ dynes/cm$^2$. The post-dosed hardening gels (after delivery) may have a rubbery consistency and have a modulus of elasticity in the range of about $1 \times 10^4$ to about $2 \times 10^6$ dynes/cm$^2$, or $1 \times 10^5$ to about $7 \times 10^5$ dynes/cm$^2$, or $2 \times 10^5$ to about $5 \times 10^5$ dynes/cm$^2$.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in the periodontal defect).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances. In some embodiments, the polymer comprises 20 wt. % to 90 wt. % of the formulation.

In various embodiments, the molecular weight of the gel can be varied by many methods known in the art. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel that includes a high molecular weight polymer tends to coagulate or solidify more quickly than a polymeric composition that includes a low-molecular weight polymer. Polymeric gel formulations that include high molecular weight polymers, also tend to have a higher solution viscosity than a polymeric gel that includes low-molecular weight polymers. In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and longer degradation time). Typically, a gel with a high molecular weight provides a stronger stent and the stent takes more time to degrade. In contrast, a gel with a low molecular weight degrades more quickly and provides a softer stent. In various embodiments, the gel has a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, and about 0.80 to about 1.00 dL/g.

In various embodiments, the stent and/or band made from a gel can have a viscosity of about 300 to about 5,000 centipoise (cp). In other embodiments, the gel can have a viscosity of from about 5 to about 300 cps, from about 10 cps to about 50 cps, or from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the stent and/or band is made from a hydrogel made of high molecular weight biocompatible elastomeric polymers of synthetic or natural origin. A desirable property for the hydrogel to have is the ability to respond rapidly to mechanical stresses, particularly shears and loads, in the oral cavity.

Hydrogels obtained from natural sources are particularly appealing because they are more likely to be biodegradable and biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly(acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the gel, microspheres may be dispersed within the gel, the microspheres being loaded with the therapeutic agent. For example, a gel may be deployed around a target tissue site (e.g., alveolar ridge). Dispersed within the gel may be a plurality of microspheres that encapsulate the desired therapeutic agent. Certain of these microspheres degrade once released from the gel, thus releasing the therapeutic agent. In some embodiments, the stent may contain microspheres comprising the therapeutic agent.

Microspheres, much like a fluid, may disperse relatively quickly, depending upon the surrounding tissue type, and hence disperse the therapeutic agent. In some situations, this may be desirable; in others, it may be more desirable to keep the therapeutic agent tightly constrained to a well-defined target site. The present invention also contemplates the use of adherent gels to so constrain dispersal of the therapeutic agent. These gels may be deployed, for example, in the oral cavity, tooth, bone or in surrounding tissue.

In some embodiments, the band or other affixing means (e.g., strip, clip, post, wire, suture, etc.) may not be biodegradable. For example, the affixing means may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. Typically, these types of affixing means may need to be removed after a certain amount of time.

Therapeutic Agents

In various embodiments, the biodegradable stent, and/or band comprises one or more therapeutic agent(s) disposed in one or more layers or homogenously throughout it.

Therapeutic agents which can be readily combined with or in the stent and/or band include, e.g., collagen, insoluble collagen derivatives, etc., and soluble solids and/or liquids dissolved therein; antiviricides; antimicrobials and/or antibiotics biocidal/biostatic sugars such as dextran, glucose, etc.; amino acids; peptides; vitamins; inorganic elements; co-factors for protein synthesis; hormones; living cells such as mesenchymal stem cells, natural extracts, genetically engineered living cells or otherwise modified living cells; DNA delivered by plasmid or viral vectors; tissue transplants; demineralized bone powder; autogenous tissues such as blood, serum, soft, bone morphogenic proteins (BMPs); osteoinductive factor; fibronectin (FN), osteonectin (ON); endothelial cell growth factor (ECGF); cementum attachment extracts (CAE); ketanserin; human growth hormone (HGH); animal growth hormones; epidermal growth factor (EGF); interleukin-1 (IL-1); human alpha thrombin; amelogenins, growth differentiation factors (e.g., GDF-5) transforming growth factor (TGF-beta); insulin-like growth factor (IGF-1); platelet derived growth factors (PDGF); fibroblast growth factors (FGF, bFGF, etc.); periodontal ligament chemotactic factor (PDLGF); somatotropin; immuno-suppressants; permeation enhancers, e.g., fatty acid esters such as laureate, myristate and stearate monoesters of polyethylene glycol, enamine derivatives, alpha-keto aldehydes, etc.; or nucleic acids. When employed, the total amount of therapeutic agent can represent from about 0.1 to about 60 weight percent of the osteoimplant.

Examples of therapeutic agents suitable for use also include, but are not limited to an anti-inflammatory agent, an analgesic agent, or an osteoinductive growth factor or an anti-microbial agent (e.g., antiviral, antibacterial, antifungal agents, etc.), or a combination thereof.

Anti-inflammatory agents include, but are not limited to, apazone, celecoxib, diclofenac, diflunisal, enolic acids (piroxicam, meloxicam), etodolac, sulindac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, tepoxalin or tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluocinolone, fluticasone or a combination thereof.

The therapeutic agent can also include anabolic growth or anti-catabolic growth factors. Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, bupivacaine, lidocaine, clonidine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

In various embodiments, the biodegradable stent, and/or band comprises one or more antimicrobial agent(s) disposed in one or more layers or homogenously throughout it to prevent microorganism growth. Anti-microbial agents to treat infection include by way of example and not limitation, antiseptic agents, antibacterial agents; quinolones and in particular fluoroquinolones (e.g., norfloxacin, ciprofloxacin, lomefloxacin, ofloxacin, etc.), aminoglycosides (e.g., gentamicin, tobramycin, etc.), glycopeptides (e.g., vancomycin, etc.), lincosamides (e.g., clindamycin), cephalosporins (e.g., first, second, third generation) and related beta-lactams, macrolides (e.g., azithromycin, erythromycin, etc.), nitroimidazoles (e.g., metronidazole), penicillins, polymyxins, tetracyclines, or combinations thereof.

Other exemplary antimicrobial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; chlorhexidine, cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

In some embodiments, the biodegradable stent, and/or band comprises one or more statins disposed in one or more layers or homogenously throughout it. Statins include, but are not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+) R and (−)-S enantiomers of the statin. In various embodiments, the statin may comprise a 1:1 racemic mixture of the statin.

In some embodiments, the therapeutic agent comprises the family of proteins known as the transforming growth factor-beta (TGFβ) superfamily of proteins, which includes the activins, inhibins, or bone morphogenetic proteins (BMPs). In some embodiments, the active agent includes at least one protein from the subclass of proteins known generally as BMPs. BMPs have been shown to possess a wide range of growth and differentiation activities, including induction of the growth and differentiation of bone, connective, kidney, heart, and neuronal tissues. See, for example, descriptions of BMPs in the following publications: BMP-2, BMP-3, BMP-4, BMP-5, BMP-6, and BMP-7 (disclosed, for example, in U.S. Pat. No. 5,013,649 (BMP-2 and BMP-4); U.S. Pat. No. 5,116,738 (BMP-3); U.S. Pat. No. 5,106,748 (BMP-5); U.S. Pat. No. 5,187,076 (BMP-6); and U.S. Pat. No. 5,141,905 (BMP-7)); BMP-8 (disclosed in PCT WO 91/18098); BMP-9 (disclosed in PCT WO 93/00432); BMP-10 (disclosed in PCT WO 94/26893); BMP-11 (disclosed in PCT WO 94/26892); BMP-12 or BMP-13 (disclosed in PCTWO 95/16035); BMP-15 (disclosed in U.S. Pat. No. 5,635,372); BMP-16 (disclosed in U.S. Pat. No. 6,331,612); MP52/GDF-5 (disclosed in PCT WO 93/16099); or BMP-17 or BMP-18 (disclosed in U.S. Pat. No. 6,027,917). The entire disclosure of these references is herein incorporated by reference. Other TGF-proteins that may be useful as the active agent of the bone cement paste include Vgr-2 and any of the growth and differentiation factors (GDFs), such as, for example, GDF-5.

A subset of BMPs that may be used in certain embodiments includes BMP-2, BMP-4, BMP-5, BMP-6, BMP-7, BMP-8, BMP-9, BMP-10, BMP-11, BMP-12 or BMP-13. In some embodiments, the composition contains two or more active agents (e.g., BMP-2 and BMP-4). Other BMPs and TGF-proteins may also be used.

The therapeutic agent may be recombinantly produced, or purified from another source. The active agent, if a TGFβ protein such as a BMP, or other dimeric protein, may be homodimeric, or may be heterodimeric with other BMPs (e.g., a heterodimer composed of one monomer each of BMP-2 and BMP-6) or with other members of the TGF-β superfamily, such as activins, inhibins and TGF-β (e.g., a heterodimer composed of one monomer each of a BMP and a related member of the TGF-β superfamily). Examples of such heterodimeric proteins are described, for example in published PCT Patent Application WO 93/09229.

In some embodiments, the amount of growth factor, (e.g., bone morphogenic protein) may be sufficient to cause bone growth. In some embodiments, the growth factor is rhBMP-2 and is contained in the stent or in bone replacement material in an amount of from 1 to 2 mg per cubic centimeter of the stent or bone replacement material. In some embodiments, the amount of rhBMP-2 morphogenic protein is from 2.0 to 2.5 mg per cubic centimeter (cc) of the stent or bone replacement material.

In some embodiments, the growth factor is supplied in a liquid carrier (e.g., an aqueous buffered solution). Exemplary aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM. In some embodiments, the BMP-2 is provided in a vehicle (including a buffer) containing sucrose, glycine, L-glutamic acid, sodium chloride, and/or polysorbate 80. The stent or bone replacement material is then soaked with it.

In some embodiments, the stent and/or band may contain additional therapeutic agents. Exemplary therapeutic agents include but are not limited to IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dithiocarbamate, and other compounds, such as, for example, sulfasalazine.

In some embodiments, the stent and/or band may comprise non-active ingredients or excipients that may have multi-functional purposes including the carrying, stabilizing and controlling the release of the therapeutic agent(s).

Exemplary excipients that may be formulated with the biodegradable stent include but are not limited to MgO (e.g., 1 wt. %), 5050 DLG 6E, 5050 DLG 1A, mPEG, TBO-Ac, mPEG, Span-65, Span-85, pluronic F127, TBO-Ac, sorbital, D-sorbitol, cyclodextrin, B-cyclodextrin, maltodextrin, pluronic F68, CaCl, 5050 7A $MgCO_3$, paraffin oil, barium sulfate, paraffin oil, glycerol monooleate, tributyl-orthoacetylcitrate (CAS: 77-90-7) (TBO-ac) or PEG 1500, Pluronic F68, 5050 PLG 7A or combinations thereof. In some embodiments, the excipients comprise from about 0.001 wt. % to about 50 wt. % of the formulation. In some embodiments, the excipients comprise from about 0.001 wt. % to about 40 wt. % of the formulation. In some embodiments, the excipients comprise from about 0.001 wt. % to about 30 wt. % of the formulation. In some embodiments, the excipients comprise from about 0.001 wt. % to about 20 wt. % of the formulation. In some embodiments, the excipients comprise from about 0.001 wt. % to about 10 wt. % of the formulation. In some embodiments, the excipients comprise from about 0.001 wt. % to about 50 wt. % of the formulation. In some embodiments, the excipients comprise from about 0.001 wt. % to about 2 wt. % of the formulation.

Bone Replacement Materials

In various embodiments, to enhance bone growth at the periodontal defect, a bone replacement material can be used in the area. Bone replacement materials can include bone particles from fully mineralized bone, and demineralized bone particles and combinations thereof. The bone particles can be autograft, allograft, xenogenic, transgenic bone particles or a combination thereof. In some embodiments, the bone replacement materials comprises collagen and/or ceramic particles.

In some embodiments, the bone replacement material includes bone cements. Bone cements are commonly provided in two or more components. The first component is usually a powder and the second component is usually in liquid form. Examples of bone cement materials include those based on acrylate materials which can react by polymerization to form acrylate polymers. Typically, a bone cement can be formed by mixing a liquid acrylate monomer with a powder such as acrylate polymer using a mixing element, where the mixing can be accomplished by hand or machine. The resulting mixture has a paste or dough-like consistency. Typically, the components of the mixture react, involving polymerization of the acrylate monomer and copolymerization with the acrylate polymer particles. The viscosity of the cement composition increases during the reaction, resulting in a hard cement. The curing reaction of a bone cement material is generally exothermic.

In some embodiments, the bone cement comprises powder that includes, for example, calcium phosphate based powders and poly-methyl-methacrylate based powders. Any of various osteoconductive powders, such as ceramics, calcium sulfate or calcium phosphate compounds, hydroxyapatite, deproteinized bone, corals, and certain polymers, can alternatively or additionally be used in the bone cement.

Typically, the bone cement is prepared prior to injection by mixing bone-cement powder (e.g., poly-methyl-methacrylate (PMMA)), a liquid monomer (e.g., methyl-methacrylate monomer (MMA)), an x-ray contrast agent (e.g., barium sulfate), and an activator of the polymerization reaction (e.g., N,N-dimethyl-p-toluidine) to form a fluid mixture. Other additives including but not limited to stabilizers, drugs, fillers, dyes and fibers may also be included in the bone cement. Since the components react upon mixing, immediately leading to the polymerization, the components of bone cement should be kept separate from each other until the user is ready to form the desired bone cement. Once mixed, the user must work very quickly because the bone cement sets and hardens rapidly.

Other examples of bone cement compositions and/or their uses are discussed in US Patent Publication No. 20080109003, U.S. Pat. Nos. 7,138,442; 7,160,932; 7,014,633; 6,752,863; 6,020,396; 5,902,839; 4,910,259; 5,276,070; 5,795,922; 5,650,108; 6,984,063; 4,588,583; 4,902,728; 5,797,873; 6,160,033; and EP 0 701 824, the disclosures of which are herein incorporated by reference.

Methods of Making Stents

Various techniques are available for forming at least a portion of a stent from the biocompatible polymer(s), therapeutic agent(s), and optional materials, including solution processing techniques and/or thermoplastic processing techniques. When solution processing techniques are used, a solvent system is typically selected that contains one or more solvent species. The solvent system is generally a good solvent for at least one component of interest, for example, the biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the stent to obtain the degradation and/or therapeutic agent release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following therapeutic agent(s) and other optional additives such as radiographic agent(s), etc. in dissolved or dispersed form. This results in a polymeric region containing these species after solvent removal.

In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the stent or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: therapeutic agent(s), radiographic agent(s), and so forth. The resulting mixture is then shaped into an implantable or affixable biodegradable stent. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, clonidine, fluocinolone and/or sulindac may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive (s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons). For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the stent. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the stent.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a stent is formed comprising PLGA or PLA polymer, a radio-opacifying agent (e.g., bismuth subcarbonate), and a therapeutic agent prone to degradation by heat and/or mechanical shear (e.g., clonidine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of the therapeutic agent (e.g., clonidine) because processing at or above these temperatures will result in substantial therapeutic agent degradation. It is further noted that in certain embodiments, the processing temperature will be below the melting point of all bioactive compounds within the composition, including the therapeutic agent. After compounding, the resulting stent is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug stent (the pre-existing drug stent can be formed using a variety of techniques including solution and thermoplastic processing techniques, and it can comprise a variety of additives including a radio-opacifying agent and/or viscosity enhancing agent), whereupon the therapeutic agent is embedded on or in the biodegradable stent. As above, the resulting solid material can then be granulated for further processing, if desired.

Typically, an extrusion process may be used to form the stent comprising a biocompatible polymer(s), therapeutic agent(s) and excipient(s). Co-extrusion may also be employed, which is a shaping process that can be used to produce a stent comprising the same or different layers or regions (for example, a structure comprising one or more polymeric matrix layers or regions that have permeability to fluids to allow immediate and/or sustained drug release). Multi-region stents can also be formed by other processing and shaping techniques such as co-injection or sequential injection molding technology.

In various embodiments, the stent that may emerge from the thermoplastic processing is cooled. Examples of cooling processes include air cooling and/or immersion in a cooling bath. In some embodiments, a water bath is used to cool the extruded stent. However, where a water-soluble therapeutic agent (e.g., clonidine, fluocinolone and/or sulindac) is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the therapeutic agent on the stent surface, thus controlling or minimizing a high drug dose "initial burst" or "bolus dose" upon implantation or insertion if this release profile is not desired.

In various embodiments, the stent can be prepared by mixing or spraying the drug with the polymer and then molding the stent to the desired shape. In various embodiments, clonidine is used and mixed or sprayed with the PLGA or PEG550 polymer, and the resulting stent may be formed by extrusion and dried.

In various embodiments, there is a stent comprising a pharmaceutical formulation comprising the therapeutic agent wherein the therapeutic agent comprises from about 5 wt. % to about 15 wt. % of the formulation or from about 1 wt. % to about 15 wt. % of the formulation, or from about 5 wt. % to about 15 wt. % of the formulation.

In some embodiments, the at least one biodegradable polymer in the stent comprises poly(lactic-co-glycolide) (PLGA) or poly(orthoester) (POE) or a combination thereof. The poly(lactic-co-glycolide) may comprise a mixture of polyglycolide (PGA) and polylactide and in some embodiments, in the mixture, there is more polylactide than polyglycolide. In various embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In some embodiments, the stent comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer is polyglycolide.

In various embodiments, the therapeutic agent's particle size is from about 5 to 30 micrometers, however, in various embodiments, it ranges from about 1 micron to 250 microns. In some embodiments, the biodegradable polymer of the stent comprises at least 50 wt. %, at least 60 wt. %, at least 70 wt. %, at least 80 wt. % of the formulation, at least 85 wt. % of the formulation, at least 90 wt. % of the formulation, at least 95 wt. % of the formulation, at least 97 wt. % of the formulation, at least 99 wt. % of the formulation.

In some embodiments, at least 75% of the particles in the stent have a size from about 10 micrometer to about 200 micrometers. In some embodiments, at least 85% of the particles in the stent have a size from about 10 micrometer to about 200 micrometers. In some embodiments, at least 95% of the particles in the stent have a size from about 10 micrometer to about 200 micrometers. In some embodiments, all of the particles in the stent have a size from about 10 micrometer to about 200 micrometers.

In some embodiments, at least 75% of the particles in the stent have a size from about 20 micrometer to about 180 micrometers. In some embodiments, at least 85% of the particles in the stent have a size from about 20 micrometers to about 180 micrometers. In some embodiments, at least 95% of the particles in the stent have a size from about 20 micrometer to about 180 micrometers. In some embodiments, all of the particles in the stent have a particle size from about 20 micrometer to about 180 micrometers.

In some embodiments, the stent comprises a pharmaceutical formulation comprising: clonidine, wherein the clonidine is in the form of a hydrochloride salt, and comprises from about 1 wt. % to about 20 wt. % of the formulation, the sulindac comprises sulindac sodium from about 5 wt. % to about 15 wt. % of the stent; and/or the fluocinolone comprises fluocinolone acetonide from about 1 wt. % to about 15 wt. % of the drug stent, and at least one biodegradable polymer, wherein the at least one biodegradable polymer comprises poly(lactide-co-glycolide) (or poly(lactic-co-glycolic acid)) or poly(orthoester) or a combination thereof, and said at least one biodegradable polymer comprises at least 80 wt. % to 90 wt % of said formulation.

In some embodiments, there are methods for treating periodontal disease. These methods comprise: administering a stent comprising a pharmaceutical composition to an organism, wherein said pharmaceutical composition comprises from about 0.05 wt. % to about 20 wt. % of the formulation, and at least one biodegradable polymer. In some embodiments, the loading is from about 5 wt. % to about 15 wt. %. In some embodiments, the loading is from about 10 wt. % to about 20 wt. %.

In some embodiment there is a higher loading of clonidine, sulindac, and/or fluocinolone, in the stent e.g., at least 20 wt. %, at least 30 wt. %, at least 40 wt. %, at least 50 wt. %, at least 60 wt. %, at least 70 wt. %, at least 80 wt. %, or at least 90 wt. %.

In some embodiments, multiple stents are affixed to the tooth or implanted around the periodontal defect to provide a strategy of triangulation at or near the periodontal defect. Thus, a plurality (at least two, at least three, at least four, at least five, at least six, at least seven, etc.) stents comprising the pharmaceutical formulations may be placed around the target tissue site (also known as the area of periodontal disease) such that the target tissue site falls within a region that is either between the formulations when there are two, or within an area whose perimeter is defined by a set of plurality of formulations.

In some embodiments, the therapeutic agent is released at a rate of 2-3 µg per day for a period of at least 3 days. In some embodiments, this release rate continues for, at least ten days, at least fourteen days, at least twenty-one days, at least thirty days, at least sixty days, at least one hundred days, at least one-hundred and thirty-five days, at least one-hundred and fifty days, or at least one hundred and eighty days. Of course the duration of treatment will depend on the severity of periodontal disease. Treatments for periodontal disease, typically can be from two weeks to two months.

In some embodiments, when the therapeutic agent comprises clonidine, the dosage may be from approximately 0.0005 to approximately 960 µg/day. Additional dosages of clonidine include from approximately 0.0005 to approximately 900 µg/day; approximately 0.0005 to approximately 500 µg/day; approximately 0.0005 to approximately 250 µg/day; approximately 0.0005 to approximately 100 µg/day; approximately 0.0005 to approximately 75 µg/day; approximately 0.001 to approximately 70 µg/day; approximately 0.001 to approximately 65 µg/day; approximately 0.001 to approximately 60 µg/day; approximately 0.001 to approximately 55 µg/day; approximately 0.001 to approximately 50 µg/day; approximately 0.001 to approximately 45 µg/day; approximately 0.001 to approximately 40 µg/day; approximately 0.001 to approximately 35 µg/day; approximately 0.0025 to approximately 30 µg/day; approximately 0.0025 to approximately 25 µg/day; approximately 0.0025 to approximately 20 µg/day; approximately 0.0025 to approximately 15 µg/day; approximately 0.0025 to approximately 10 µg/day; approximately 0.0025 to approximately 5 µg/day; and approximately 0.0025 to approximately 2.5 µg/day. In another embodiment, the dosage of clonidine is from approximately 0.005 to approximately 15 µg/day. In another embodiment, the dosage of clonidine is from approximately 0.005 to approximately 10 µg/day. In another embodiment, the dosage of clonidine is from approximately 0.005 to approximately 5 µg/day. In another embodiment, the dosage of clonidine is from approximately 0.005 to 2.5 µg/day. In some embodiments, the amount of clonidine is between 40 and 600 µg/day. In some embodiments, the amount of clonidine is between 200 and 400 µg/day.

In some embodiments, when the stent comprises fluocinolone, the dosage of fluocinolone may be from approximately 0.0005 to approximately 100 µg/day. Additional dosages of fluocinolone include from approximately 0.0005 to approximately 50 µg/day; approximately 0.0005 to approximately 25 µg/day; approximately 0.0005 to approximately 10 µg/day; approximately 0.0005 to approximately 5 µg/day; approximately 0.0005 to approximately 1 µg/day; approximately 0.005 to approximately 0.75 µg/day; approximately 0.0005 to approximately 0.5 µg/day; approximately 0.0005 to approximately 0.25 µg/day; approximately 0.0005 to approximately 0.1 µg/day; approximately 0.0005 to approximately 0.075 µg/day; approximately 0.0005 to approximately 0.05 µg/day; approximately 0.001 to approximately 0.025 µg/day; approximately 0.001 to approximately 0.01 µg/day; approximately 0.001 to approximately 0.0075 µg/day; approximately 0.001 to approximately 0.005 µg/day; approximately 0.001 to approximately 0.025 µg/day; and 0.002 to approximately 0.025 µg/day. In another embodiment, the dosage of fluocinolone is from approximately 0.001 to approximately 15 µg/day. In another embodiment, the dosage of fluocinolone is from approximately 0.001 to approximately 10 µg/day. In another embodiment, the dosage of fluocinolone is from approximately 0.001 to approximately 5 µg/day. In another embodiment, the dosage of fluocinolone is from approximately 0.001 to 2.5 µg/day. In some embodiments, the amount of fluocinolone is between 40 and 600 µg/day. In some embodiments, the amount of fluocinolone is between 200 and 400 µg/day.

In some embodiments, there is sufficient fluocinolone such that the fluocinolone is released at a rate of 2-3 µg per day for a period of at least three days. In some embodiments, this release rate continues for, at least ten days, at least fourteen days, at least twenty-one days, at least thirty days, at least fifty days, at least sixty days, at least one hundred days, at least one-hundred and thirty-five days, at least one-hundred and fifty days, or at least one hundred and eighty days.

In some embodiments, when the stent comprises sulindac, it is released at a rate of 5-15 mg/per day, or 7-12 mg/day or 8-10 mg/day for a period of at least two weeks to two months. In some embodiments, this release rate lasts for, at least thirty days, at least sixty days, at least one hundred days, at least one-hundred and thirty-five days, at least one-hundred and fifty days, or at least one hundred and eighty days.

In one embodiment, the sulindac dosage is from approximately 0.001 µg/day to approximately 100 mg/day. Additional dosages of sulindac can include from approximately 0.001 µg/day to approximately 200 mg/day; approximately 0.001 µg/day to approximately 100 mg/day; approximately 0.001 µg/day to approximately 1 mg/day; approximately 0.001 µg/day to approximately 500 µg/day; approximately 0.001 µg/day to approximately 100 µg/day; approximately 0.025 to approximately 75 µg/day; approximately 0.025 µg/day to approximately 65 µg/day; approximately 0.025 µg/day to approximately 60 µg/day; approximately 0.025 µg/day to approximately 55 µg/day; approximately 0.025 µg/day to approximately 50 µg/day; approximately 0.025 µg/day to approximately 45 µg/day; approximately 0.025 µg/day to approximately 40 µg/day; approximately 0.025 µg/day to approximately 35 µg/day; approximately 0.005 to approximately 30 µg/day; approximately 0.005 to approximately 25 µg/day; approximately 0.005 µg/day to approximately 20 µg/day; and approximately 0.005 µg/day to approximately 15 µg/day. In another embodiment, the dosage of sulindac is from approximately 0.01 µg/day to approximately 15 µg/day. In another embodiment, the dosage of sulindac is from approximately 0.01 µg/day to approximately 10 µg/day. In another embodiment, the dosage of sulindac is from approximately 0.01 µg/day to approximately 5 µg/day. In another embodiment, the dosage of sulindac is from approximately 0.01 µg/day to approximately 20 µg/day. In another embodiment, sulindac is administered in a stent that releases 9.6 µg/day.

In some embodiments, there is a method for selectively guided tissue regeneration in treating a periodontal defect adjacent to a root of a tooth, the method comprising affixing a biodegradable stent that maintains a space between gingival epithelium tissue and periodontal ligament tissue to the tooth, the biodegradable stent comprising a coronal portion and a transverse portion, the coronal portion having a first surface configured to contact at least a portion of the root of the tooth and a second surface configured to contact at least a portion of the periodontal defect, the transverse portion above the coronal portion and substantially perpendicular to it, the transverse portion having a first surface configured to contact a portion of the tooth and a second surface configured to extend away from the tooth and over a portion of the periodontal defect, wherein the biodegradable stent reduces ingrowth of gingival epithelium cells and permits ingrowth of periodontal ligament cells.

In some embodiments, in use for the treatment of periodontal disease, (a) a sharp dissection of the gum tissues overlying the bony defect component of the periodontal lesion is made, (b) debridement of the periodontal lesion is then performed, which results in an exposed bony pocket; (c) the stent is then placed at or near the exposed boney pocket, (d) the periodontal lesion is optionally filled with bone replacement material (e.g., bone graft material), and (e) the gum tissue can be closed by suturing the gum tissue in apposition to the stent such that the transverse portion of the stent is visible in the mouth and above the margin of gum line or the gum tissue can be pulled over the transverse portion of the stent and sutured in apposition to the tooth itself.

In some embodiments, there is a method for selectively guided tissue regeneration, wherein soft tissue is separated from at least a portion of the tooth root located at the periodontal defect before the biodegradable stent is affixed to the tooth.

In some embodiments, a method is provided where the practitioner affixes the stent to the tooth by applying an adhesive to it and then attaches an elastic band around the tooth to further hold the stent in place against the tooth. The elastic band can be changed at a later time.

Kits

One or more of the stents, and/or bands may be placed in a kit, which may be sterilizable by radiation in a terminal sterilization step in the final packaging. Terminal sterilization of a product provides greater assurance of sterility than from processes such as an aseptic process, which require individual product components to be sterilized separately and the final package assembled in a sterile environment. In various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, the stents and/or bands may be packaged in a moisture resistant kit and then terminally sterilized by gamma irradiation. In use the practitioner removes the one or all components from the sterile package for use. In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize delivery device and/or one or more of its components (e.g., stents, bands, therapeutic agents), including, but not limited to, gas sterilization, such as, for example, with ethylene oxide or steam sterilization.

In various embodiments, a kit is provided comprising sterile or non-sterile stents. The kit may include additional parts along with the stents combined together to be used with it (e.g., wipes, needles, syringes, etc.). The kit may include gloves, drapes, wound dressings and other procedural supplies for maintaining sterility of the delivery process, as well as an instruction booklet, DVDs, or CDs, which may include a chart that shows how to use the stents.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A biodegradable stent for selectively guided tissue regeneration in treating a periodontal defect adjacent to a root of a tooth, the biodegradable stent comprising a porous coronal portion having a pore size between about 10 µm to about 200 µm and a non-porous transverse portion, the coronal portion having a first surface configured to contact at least a portion of the root of the tooth, the first surface having a zone configured to immediately release a therapeutic agent, the therapeutic agent comprising clonidine, the coronal portion having a second surface configured to contact at least a portion of the periodontal defect, the second surface having a zone configured to provide sustained release of the therapeutic agent, the transverse portion above the coronal portion and substantially perpendicular to it, the transverse portion having a first surface configured to contact a portion of the tooth and a second surface configured to extend away from the tooth and over a portion of the periodontal defect to maintain a space between gingival epithelium tissue and periodontal ligament tissue, wherein the biodegradable stent reduces ingrowth of gingival epithelium cells and permits ingrowth of periodontal ligament cells, wherein all of the first surface of the coronal portion conforms to the tooth and/or tooth root, and the stent comprises a hardening gel having a pre-dosed modulus of elasticity of about $1 \times 10^4$ to about $3 \times 10^5$ dynes/cm$^2$ and a post-dosed modulus of elasticity between about $1 \times 10^4$ to about $2 \times 10^6$ dynes/cm$^2$ and the stent comprises a plasticizer comprising mPEG, and is configured to attach to the tooth by an elastic band coated with an adhesive and comprising the therapeutic agent.

2. A biodegradable stent according to claim 1, wherein the coronal portion is longer than the transverse portion and the transverse portion comprises a shelf.

3. A biodegradable stent according to claim 1, wherein the coronal portion and/or transverse portion are porous to periodontal ligament cells and cementoblasts and non-porous to gingival epithelium cells.

4. A biodegradable stent according to claim 1, wherein the biodegradable stent is affixed lateral and mesial to the tooth to prevent ingrowth of gingival epithelium cells or the biodegradable stent is one piece.

5. A biodegradable stent according to claim 1, wherein the first surface of the coronal portion and/or the first surface of the transverse portion comprise an adhesive to affix the first surface to the tooth or tooth root.

6. A biodegradable stent according to claim 1, wherein the biodegradable material comprises collagen, a hydrogel, a synthetic polymer, or a combination thereof.

7. A biodegradable stent according to claim 6, wherein the polymer comprises one or more of collagen, poly(lactide-co-glycolide) (PLGA), polylactide (PLA), polyglycolide (PGA), D-lactide, D,L-lactide, L-lactide, D,L-lactide-co-ε-caprolactone, D,L -lactide-co-glycolide-co-ε-caprolactone or a combination thereof.

8. A biodegradable stent according to claim 1, wherein the therapeutic agent further comprises an antimicrobial agent, a growth factor, or a combination thereof.

9. A biodegradable stent according to claim 1, wherein the stent is further attached to the tooth by a strip, wire, clip or a suture that is coated with an adhesive and the band, strip, wire, clip or suture can be biodegradable or non-biodegradable.

10. A biodegradable stent according to claim 1, wherein the therapeutic agent further comprises sulindac, fluocinolone or a combination thereof.

11. A biodegradable stent for selectively guided tissue regeneration in treating a periodontal defect adjacent to a root of a tooth, the biodegradable stent comprising a porous coronal portion having a pore size between about 10 µm to about 200 µm and a non-porous transverse portion, the coronal portion having a first surface configured to contact at least a portion of the root of the tooth, the first surface having a zone configured to release a therapeutic agent, the therapeutic agent comprising clonidine, the coronal portion having a second surface configured to contact at least a portion of the periodontal defect, the second surface having a zone configured to provide sustained release of the therapeutic agent, the transverse portion above the coronal portion and substantially perpendicular to it, the transverse portion having a first surface configured to contact a portion of the tooth and a second surface configured to extend away from the tooth and over a portion of the periodontal defect to maintain a space between gingival epithelium tissue and periodontal ligament tissue, an elastic band coated with an adhesive and comprising the therapeutic agent extending over the tooth and contacting the second surface of the coronal portion and/or the transverse portion of the biodegradable stent so as to hold the biodegradable stent in place, wherein the biodegradable stent reduces ingrowth of gingival epithelium cells and permits ingrowth of periodontal ligament cells, wherein all of the first surface of the coronal portion conforms to the tooth and/or tooth root, and the stent comprises a hardening gel having a pre-dosed modulus of elasticity of about $1 \times 10^4$ to about $3 \times 10^5$ dynes/cm$^2$ and a post-dosed modulus of elasticity between about $1 \times 10^4$ to about $2 \times 10^6$ dynes/cm$^2$ and the stent comprises a plasticizer comprising mPEG.

12. A biodegradable stent according to claim 11, wherein the coronal portion is longer than the transverse portion and the transverse portion comprises a shelf.

13. A biodegradable stent according to claim 11, wherein the band prevents bacterial growth and/or is a removable non-biodegradable elastic band.

14. A biodegradable stent according to claim 11, wherein the biodegradable stent is affixed lateral and mesial to the tooth to prevent ingrowth of gingival epithelium cells but allows growth of the periodontal ligament both horizontally and vertically.

15. A biodegradable stent according to claim 11, wherein the first surface of the coronal portion and/or the first surface of the transverse portion comprise an adhesive to secure the first surface to the tooth or tooth root.

16. A biodegradable stent according to claim 11, wherein the band comprises one or more regions containing the therapeutic agent comprising an antimicrobial agent, a growth factor, an analgesic, an anti-inflammatory agent, or a combination thereof.

17. A method for selectively guided tissue regeneration in treating a periodontal defect adjacent to a root of a tooth, the method comprising affixing a biodegradable stent that maintains a space between gingival epithelium tissue and periodontal ligament tissue to the tooth, the biodegradable stent comprising a porous coronal portion having a pore size between about 10 µm to about 200 µm and a non-porous transverse portion, the coronal portion having a first surface configured to contact at least a portion of the root of the tooth, the first surface having a zone configured to immediately release a therapeutic agent and a second surface configured to contact at least a portion of the periodontal defect, the second surface having a zone configured to provide sustained release of the therapeutic agent, the therapeutic agent comprising clonidine, the transverse portion above the coronal portion and substantially perpendicular to it, the transverse portion having a first surface configured to contact a portion of the tooth and a second surface configured to extend away from the tooth and over a portion of the periodontal defect, wherein the biodegradable stent reduces ingrowth of gingival epithelium cells and permits ingrowth of periodontal ligament cells, wherein all of the first surface of the coronal portion conforms to the tooth and/or tooth root, and the stent comprises a hardening gel having a pre-dosed modulus of elasticity of about $1 \times 10^4$ to about $3 \times 10^5$ dynes/cm$^2$ and a post-dosed modulus of elasticity between about $1 \times 10^4$ to about $2 \times 10^6$ dynes/cm$^2$ and the stent comprises a plasticizer comprising mPEG and the biodegradable stent comprises a plasticizer, and attaching the stent to the tooth by an elastic band coated with an adhesive and comprising the therapeutic agent.

18. A method for selectively guided tissue regeneration according to claim 17, wherein separating soft tissue from at least a portion of the tooth root located at the periodontal defect before the biodegradable stent is affixed to the tooth.

19. A method for selectively guided tissue regeneration according to claim 17, wherein attaching the band over the tooth so as to allow contact with the second surface of the coronal portion and/or the transverse portion of the stent to hold the stent in place.

* * * * *

UNITED STATES PATENT AND TRADEMARK OFFICE
CERTIFICATE OF CORRECTION

PATENT NO. : 9,526,600 B2
APPLICATION NO. : 12/839940
DATED : December 27, 2016
INVENTOR(S) : Drapeau et al.

Page 1 of 1

It is certified that error appears in the above-identified patent and that said Letters Patent is hereby corrected as shown below:

On the Title Page

Page 2, in item (56), under "U.S. PATENT DOCUMENTS", in Column 1, Line 17, delete "Shalaby" and insert -- Shalaby et al. --, therefor.

In the Specification

In Column 10, Line 41, delete "periodontal ligament 64" and insert -- periodontal ligament 66 --, therefor.

Signed and Sealed this
Fourth Day of April, 2017

Michelle K. Lee
*Director of the United States Patent and Trademark Office*